(12) United States Patent
Oberreiter et al.

(10) Patent No.: US 9,744,375 B2
(45) Date of Patent: Aug. 29, 2017

(54) APPARATUS AND METHODS FOR CONTROLLING AND APPLYING FLASH LAMP RADIATION

(71) Applicants: Richard Oberreiter, Newport Beach, CA (US); Jan Enemaerke, San Marcos, CA (US)

(72) Inventors: Richard Oberreiter, Newport Beach, CA (US); Jan Enemaerke, San Marcos, CA (US)

(73) Assignee: Allergia, Inc., San Marcos, CA (US)

( * ) Notice: Subject to any disclaimer, the term of this patent is extended or adjusted under 35 U.S.C. 154(b) by 22 days.

(21) Appl. No.: 14/223,861

(22) Filed: Mar. 24, 2014

(65) Prior Publication Data

US 2014/0207214 A1    Jul. 24, 2014

Related U.S. Application Data

(62) Division of application No. 13/198,672, filed on Aug. 4, 2011, now abandoned.
(Continued)

(51) Int. Cl.
*A61B 19/00* (2006.01)
*A61N 5/06* (2006.01)
*A61B 90/00* (2016.01)

(52) U.S. Cl.
CPC ...... *A61N 5/0603* (2013.01); *A61B 2090/049* (2016.02); *A61B 2090/065* (2016.02);
(Continued)

(58) Field of Classification Search
CPC .... A61N 2005/0607; A61N 2005/0644; A61N 5/0603; A61N 2005/063; A61N 5/0622;
(Continued)

(56) References Cited

U.S. PATENT DOCUMENTS

| 7,226,470 B2* | 6/2007 | Kemeny | A61N 5/0603 |
| | | | 128/898 |
| 7,351,253 B2* | 4/2008 | DiMauro | A61N 5/0603 |
| | | | 128/898 |

(Continued)

*Primary Examiner* — Ahmed Farah
(74) *Attorney, Agent, or Firm* — J. Mark Holland & Assoc.; J. Mark Holland; Alison Adnan

(57) ABSTRACT

Apparatus and methods are disclosed for treating allergic rhinitis (seasonal and perennial hay fever), by application of flash lamp radiation. The nasal cavity can be illuminated in a safe and effective manner, with non-coherent light from a flash-lamp or other suitable source. This illumination can be accomplished in any suitable manner, including by use of a handheld device. Such handheld embodiments may contain a power source (battery or AC), control circuitry, light source (flash-lamp or diode laser), lens (focusing or non-focusing), light filter, and/or fiber-optic for delivering light to the nasal cavity. Embodiments include using any suitable light energy, such as visible light in the red wavelengths with a power output of 1 to 10 Joules per $cm^2$. The device can be pre-programmed to deliver a specified amount of light in a specified amount of time using multiple pulses (in the case of a flash lamp) or a continuous wave (in the case of a diode laser). In many useful embodiments, a rigid fiber-optic extends from the lens/light filter a length of 10 to 20 mm, although it can be any convenient and useful size and shape. Contact sensors can be arrayed on the device for various purposes, such as to restrict illumination to times when the fiber optic is inserted into the nasal cavity. This and/or other safety features can prevent the high-intensity light from being fired into open space, a person's eyes, and/or otherwise causing a potential vision or other hazard. Preferably, the device can be easily and comfortably inserted into a nostril. The fiber-optic can be angled (either in its own shape or by the user manipulating it to a convenient angle/position) so as to allow the user to easily grip the device and insert the fiber-optic without having to use a mirror or other aid. Light (Continued)

from the device can be emitted at a specified light frequency that causes a desired immunosuppressive response in the cellular system.

6 Claims, 5 Drawing Sheets

Related U.S. Application Data

(60) Provisional application No. 61/371,172, filed on Aug. 5, 2010.

(52) U.S. Cl.
CPC .............. *A61N 2005/0607* (2013.01); *A61N 2005/0626* (2013.01); *A61N 2005/0654* (2013.01); *A61N 2005/0662* (2013.01)

(58) Field of Classification Search
CPC .......... A61N 5/0624; A61N 2005/0635; A61N 2005/0643
USPC ... 607/88–96, 100–102, 108, 109, 136, 137; 606/3, 13–19; 128/898
See application file for complete search history.

(56) References Cited

U.S. PATENT DOCUMENTS

| | | | | |
|---|---|---|---|---|
| 8,109,981 | B2* | 2/2012 | Gertner | A61N 5/0603 606/13 |
| 8,167,920 | B2* | 5/2012 | DiMauro | A61B 17/688 128/898 |
| 8,721,696 | B2* | 5/2014 | Krespi | A61N 5/0601 607/100 |
| 9,265,967 | B2* | 2/2016 | Bouboulis | A61N 5/0603 |
| 2004/0030368 | A1* | 2/2004 | Kemeny | A61N 5/0603 607/88 |
| 2005/0107853 | A1* | 5/2005 | Krespi et al. | 607/89 |
| 2006/0047329 | A1* | 3/2006 | Krespi et al. | 607/86 |
| 2010/0160838 | A1* | 6/2010 | Krespi | 601/15 |
| 2011/0021971 | A1* | 1/2011 | Krespi | A61N 5/0601 604/20 |

\* cited by examiner

APPARATUS AND METHODS FOR CONTROLLING AND APPLYING FLASH LAMP RADIATION

CROSS-REFERENCE TO RELATED APPLICATIONS

This divisional application claims priority to U.S. patent application Ser. No. 13/198,672, filed on Aug. 4, 2011, which was based on U.S. Provisional Application Ser. No. 61/371,172, filed Aug. 5, 2010, the disclosure of which is incorporated herein by reference in its entirety.

FIELD OF THE INVENTION

The general field of the invention is medicine and the use of flash lamp radiation, and more specifically, the use of phototherapy to treat the symptoms of seasonal and perennial allergic rhinitis.

BACKGROUND OF THE INVENTION

Allergic rhinitis (also commonly known as hay fever) is a condition that occurs when allergens such as pollens cause an inflammation of mucous membranes in the nose, with symptoms including sneezing, itching, nasal discharge, and/or congestion. Perennial and seasonal allergic rhinitis afflict millions of persons throughout the world.

Treatment of allergic rhinitis has traditionally been accomplished through the use of systemic medications, antihistamines, decongestants, steroids, and long-term immunotherapy. Each of these treatment modalities has advantages and disadvantages, but typically no single modality or combination of modalities can completely relieve all of the symptoms of allergic rhinitis.

In contrast to (and/or as a supplement to) those traditional treatments, phototherapy relatively recently has been found to be effective in treating allergic rhinitis. Although phototherapy has been used for many years to treat various skin conditions (such as acne, psoriasis, pigmented lesions, and wounds, and to help tighten sagging skin, reduce wrinkles, and stimulate circulation, to name a few), and lasers have been used in surgical applications (including to treat various conditions in the nasal cavity such as lesions, polyps etc.), studies have recently shown that phototherapy can also be used to help temporarily reduce or eliminate the symptoms of allergic rhinitis. The present invention provides a convenient, safe, and affordable way for making available that treatment.

SUMMARY OF THE INVENTION

For the purpose of summarizing the invention, certain objects and advantages have been described herein. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The invention described herein preferably utilizes phototherapy in the treatment of allergic rhinitis. In certain embodiments, the invention stimulates the human body's own respiratory system to reduce the symptoms of allergic rhinitis.

The typical human allergic response in the respiratory tract is characterized by two phases of the immune system. In the initial phase, after an allergen challenge is presented to the body (e.g. via the inhalation of dust, pollen, dust, or other allergens), resident mast cells in the nose and bronchi degranulate to release histamine as well as other vasoactive mediators (such as prostaglandins, leukotriens, etc.). These mediators typically cause localized itching and swelling of tissue, as well as an increase in mucus production.

In the second phase of the allergic response, a myriad of inflammatory cells (such as activated T cells, eosinophils and basophils) are recruited to the inflammatory site. These inflammatory cells serve to further inflame the local tissues, and typically perpetuate the inflammatory response for as long as the allergen is present. Allergy sufferers are familiar with these symptoms (itching and swelling of tissues, increased mucus production, etc.).

Studies have shown that those phases of the allergic response can be beneficially inhibited (to relieve the allergy sufferer) by the application of phototherapy, and that phototherapy can have profound immunosuppressive effects in such applications. In one such study, phototherapy significantly reduced the number of eosinophils and T cells by inducing apoptosis through a light-mediated alteration in Ca+ metabolism within these cells. Furthermore, phototherapy inhibited the release of histamines from basophils and mast cells. In short, these studies indicate that application of phototherapy can improves clinical symptoms such as sneezing, rhinorrhea (runny nose), nasal itching, and nasal congestion.

Preferably, the invention provides various apparatus and methods of treating the symptoms of seasonal allergic rhinitis and perennial allergic rhinitis. Preferably, the embodiments of the invention include using a convenient and economic device to allow sufferers to be treated by a series of steps such as the following, to treat their allergic rhinitis:

1. Illuminating the nasal cavity with light in (or including) the wavelength of approximately 600 nm to 700 nm (generally red light). The light can conveniently be generated by a Xenon flash lamp, diode laser, or other suitable means.

2. Delivering that desired light in a quantity that is safe but effective (such as in the range of approximately at least 1 and up to 10 Joules/cm$^2$ of light energy). Persons of ordinary skill in the art will understand that the total energy delivered needs to be sufficiently large to produce the desired result, but sufficiently small to ensure that the patient's tissues are not burned or otherwise damaged by the treatment. Preferably, the desired light energy is delivered via a series of non-thermal narrow-band emissions from the device in order to ensure a phototherapeutic effect while simultaneously preventing tissue damage.

3. Delivering the light produced by the device into the nasal cavity in a controlled manner to a desired location within the nasal cavity. Preferably, this is done using a rigid or flexible fiber optic inserted into the nasal cavity, and the fiber optic preferably has a length approximately in the range of 0 to 20 mm. Persons of ordinary skill in the art will understand that the precise elements, configuration, and dimensions of the delivery system can vary according to the application, the size of the patient, and other factors, and that certain elements of the delivery apparatus can be provided in modular form to allow ready replacement, customization, and/or other benefits.

A wide variety of apparatus (including those described herein) can be used to deliver the radiation and accomplish the desired methods and medical treatments. These and other embodiments will become readily apparent to those skilled in the art from the following detailed description of the preferred embodiments having reference to the attached figures, the invention not being limited to any particular preferred embodiment(s) disclosed.

DETAILED DESCRIPTION

Figure 1:
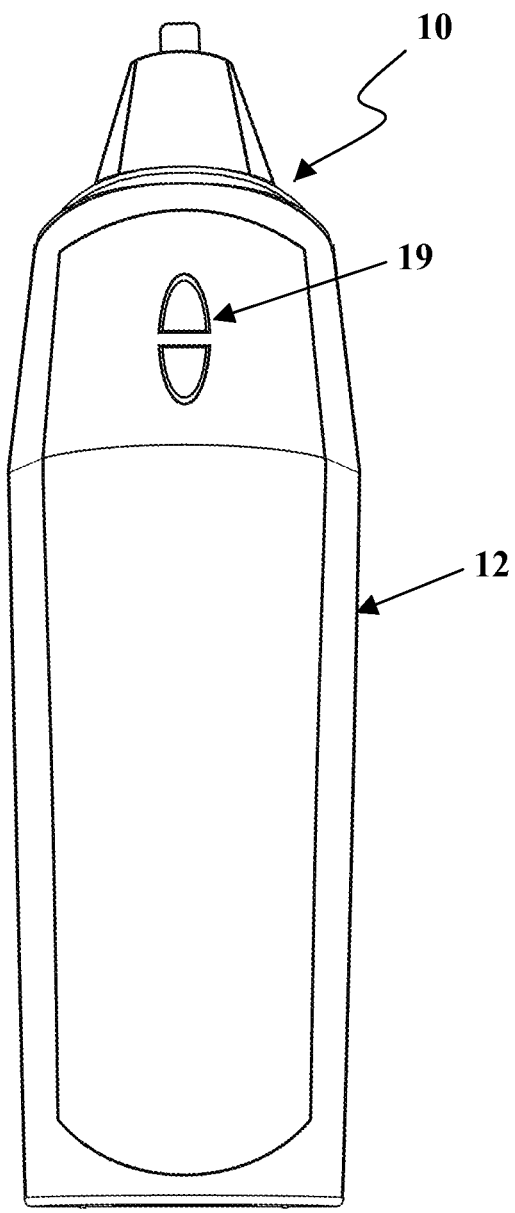
FIG. 1 is a back elevation view of one embodiment of the apparatus of the invention.
Figure 2:
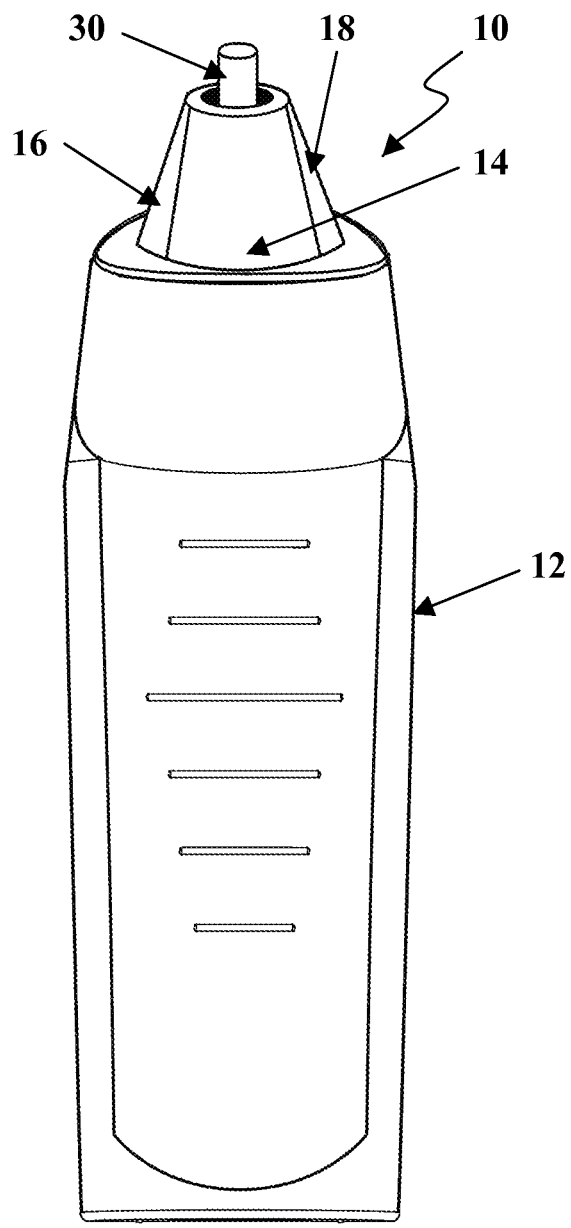
FIG. 2 is a front elevation view of the embodiment of FIG. 1.
Figure 3:
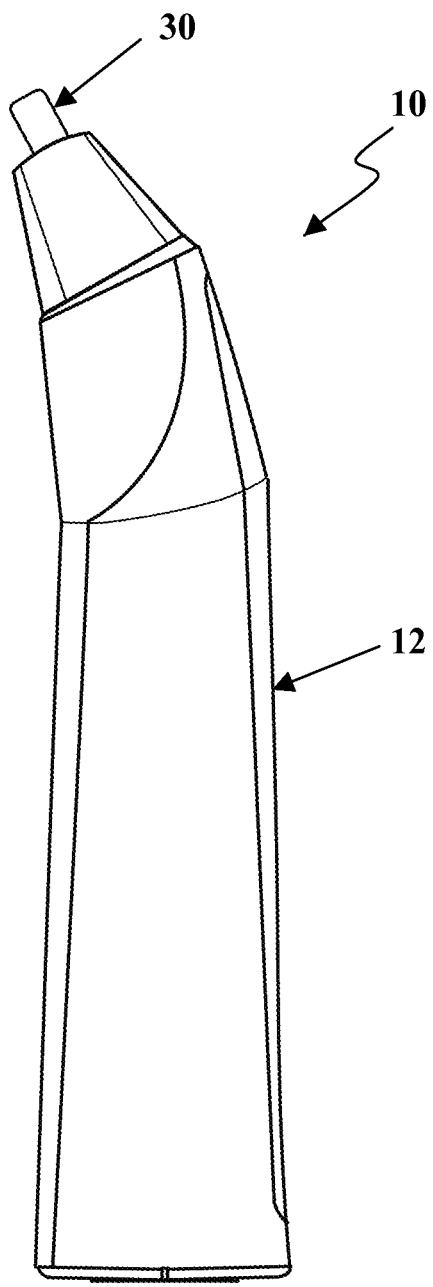
FIG. 3 is a side elevation view of the embodiment of FIG. 1.
Figure 4:
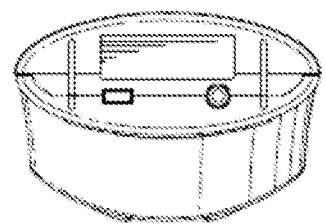
FIG. 4 is a bottom view of the embodiment of FIG. 1.
Figure 5A:
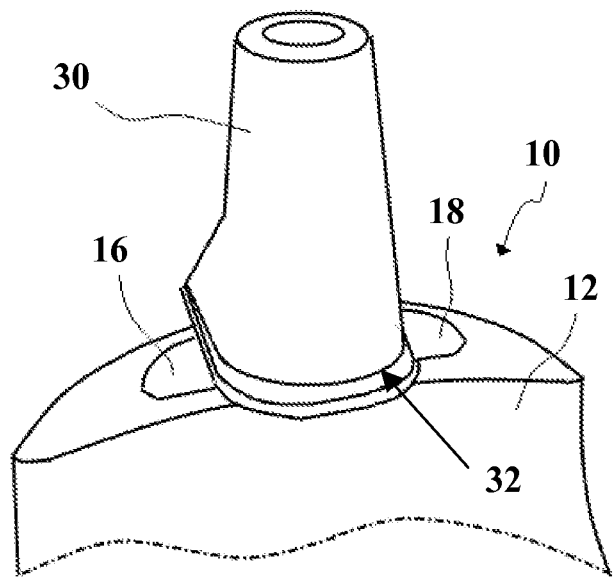
FIGS. 5A and 5B are similar to the top portion of FIG. 1, but each shows a perspective view (including one of the many optic elements 30 that may be used to practice the invention) of a separate further embodiment of the many different embodiments in which the invention may be practiced.
Figure 5B:
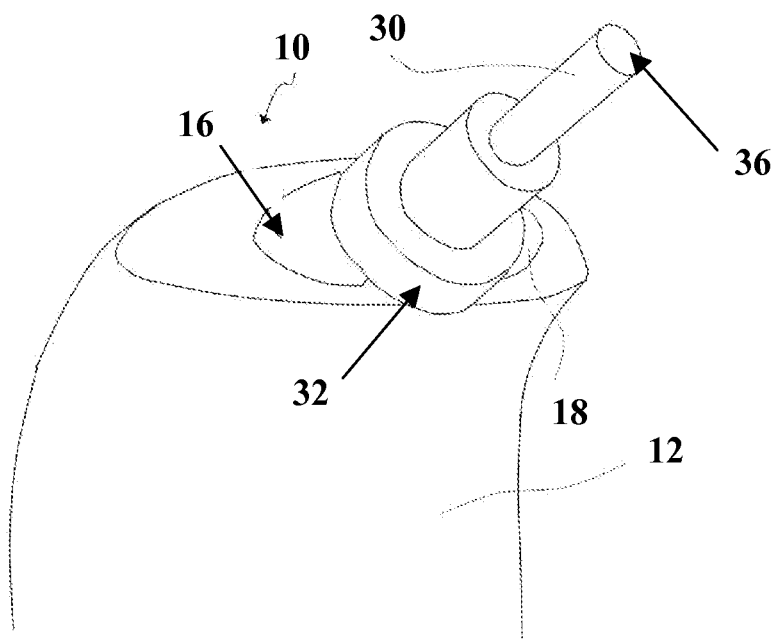

Embodiments of the present invention will now be described with references to the accompanying Figures, wherein like reference numerals refer to like elements throughout. The terminology used in the description presented herein is not intended to be interpreted in any limited or restrictive manner, simply because it is being utilized in conjunction with a detailed description of certain embodiments of the invention. Furthermore, various embodiments of the invention (whether or not specifically described herein) may include novel features, no single one of which is solely responsible for its desirable attributes or which is essential to practicing the invention herein described.

Figure 6:
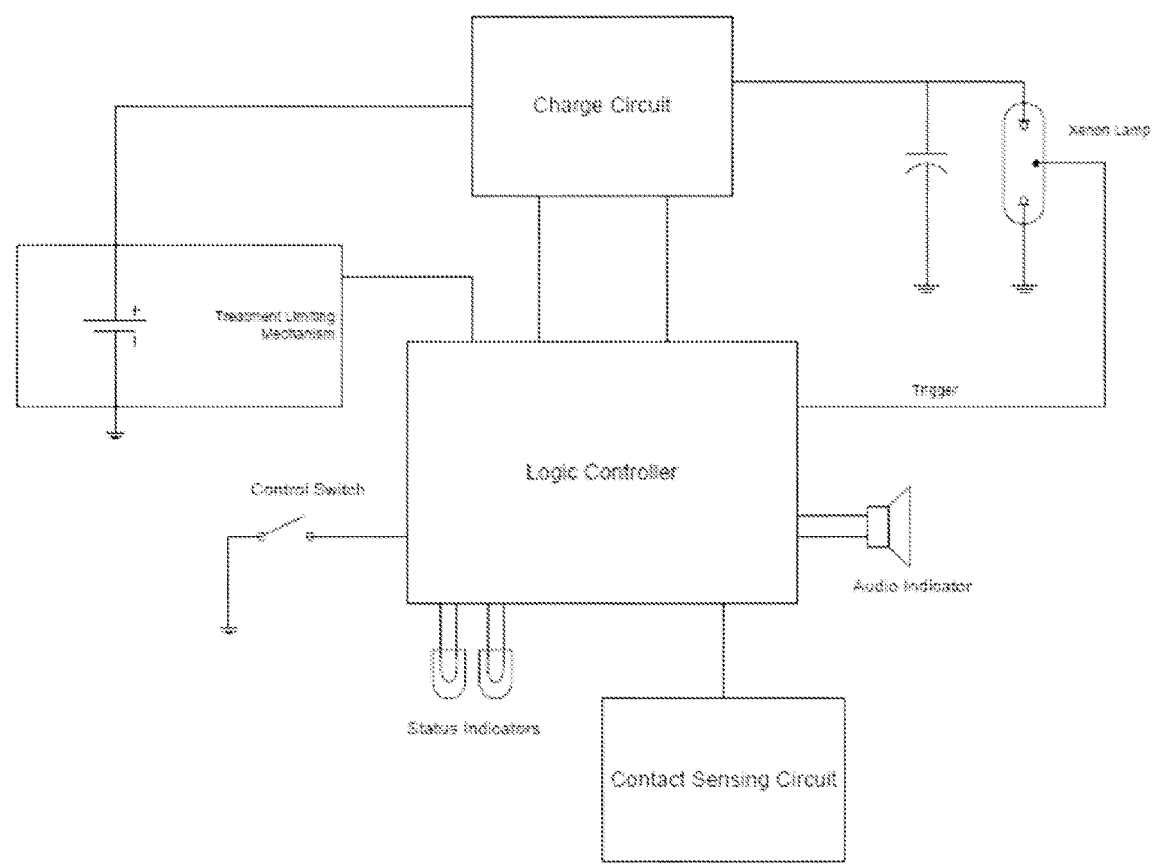
FIG. 6 is a basic schematic of one embodiment of circuitry that can be used to practice the invention.

One of the many embodiments of the device is a handheld device, such as shown in FIGS. 1-5. Preferably, the handheld device 10 is fully self-contained with a housing 12 having within it a battery power source (not shown) and control circuitry (exemplary circuitry is illustrated in FIG. 6 and includes certain of the components and/or functions discussed here, but persons of ordinary skill in the art will understand that a wide variety of different circuitry and/or components thereof may be utilized without departing from the scope of the invention). The device 10 further preferably includes a control button or sensor 19 by which a user can activate the device (to execute a pre-programmed flashing light sequence from the flash lamp and/or activate other treatment or action or otherwise control the device 10). The device 10 preferably also includes one or more safety sensors 16 and 18 and a fiber optic 30 (see FIG. 5) to deliver the light energy to the targeted tissues.

The light source can be any of a wide range of sources, including by way of example a Xenon flash lamp 14 of suitable size and power. As with all of the components of any handheld embodiment, the lamp preferably is suitably lightweight and is fabricated from suitably durable, non-toxic materials. Persons of ordinary skill in the art will understand that this and the other elements described herein may be fabricated from a wide range of suitable materials and processes, all without departing from the spirit and scope of the invention.

Preferably, the light source 14 is controlled by a suitable circuit system (see the example of FIG. 6). Persons of ordinary skill in the art will understand that the control circuit preferably will contains either a logic circuit or software suitable to (a) charge the electrical system and (b) deliver a desired dose of radiation. In various embodiments, the dosage can be pre-programmed as a selected and/or selectable number of light flashes at a selected/selectable rate and frequency. Again preferably, the device 10 is configured to deliver a safe and effective dosage to the nasal cavity (approximately 1 to 10 Joules/cm$^2$, or whatever other dosage provides the desired efficacy without being so large as to damage or discomfort the patient) via non-thermal narrow-band emissions.

In certain embodiments, one or more safety contact sensors 16 and 18 can be provided. Preferably, and among other things, these sensors are designed to prevent the device 10 from producing light flashes when the fiber optic is in open space (rather than inside a user's nostril), to prevent temporary or permanent vision impairment or other undesired results.

Persons of ordinary skill in the art will understand that such safety sensors can be provided in any of a wide variety of suitable forms. One of the many examples of a safety sensor is conveniently viewable in FIGS. 2, 5A, and 5B, as elements 16 and 18. Such an embodiment requires that two or more electrical capacitance or impedance sensors 16 and 18 be positioned so that they will contact the user's skin or similar tissue around the entrance to the nasal cavity before the flash-lamp 14 is allowed to fire. These sensors could be arranged as shown in the aforementioned Figures or in any suitable position and configuration (for example, on a ring below the fiber optic element).

Another example of such safety sensors can include a pressure switch or electrical contact switch (not shown) that has to be closed before the flash-lamp 14 is allowed to fire. Such a switch can be positioned at any suitable location, including by way of example in a two part ring around the optic element that is pressed together (or as part of a two part mechanism that slides inside of each other) when the user inserts the optic element into the user's nostril. In other words, the necessary contact can be made when the user presses down on a ring or flange as part of the procedure to fire the flash-lamp. Alternatively, the "safety" switch or sensor could be activated in some way other than by contact with tissue near the user's nostril (such as by a separate button push or other action by the user).

Yet, another example of a safety sensor system can include a light sensor (not shown) that would detect a low to no-light conditions before the flash lamp 14 is allowed to fire. The light sensor or distal end of a fiber optic leading back to a light sensor can be positioned at the distal end of the fiber optic applicator 30. In order for the light sensor to detect a low to no-light it would have to be inside of the nasal passage. If the light sensor was outside of the nasal passage it would detect ambient or normal light levels and prevent the flash-lamp from firing, thus avoiding the possibility of accidental discharge of the flash-lamp in the open.

The invention further preferably includes one or more elements to deliver the energy to the desired location. Again, persons of ordinary skill in the art will understand that any suitable apparatus can be used. In FIG. 5, for example, a fiber optic applicator 30 preferably includes a base end 32 located near the flash-lamp 14 (in a relationship that facilitates the desired transmission of energy from the lamp 14 to the tissue receiving the phototherapy treatment). Preferably, the fiber optic is long enough to comfortably fit within the outer nasal cavity (like the tip of a nasal spray applicator). A convenient length that can be used for a significant portion of the human population is in the range of 10 mm to 20 mm.

Also preferably, the fiber optic element is rigid, to ensure controlled positioning and provide other benefits. It preferably also has an opaque coating on its exterior surface (except at the ends), to minimize loss of the energy during transmission and to help focus the energy transmission from the lamp source 14 to the distal end 36 of the optic element.

The distal end 36 of the fiber optic 30 (that is placed inside the user's nasal cavity during application of the phototherapy) can have a wide variety of different shapes. Among other things, factors in the design of such shape include, without limitation, the comfort of the user, optimizing and controlling dispersion of the light energy, and others. Suitable shapes include, but are not limited to, a convex shape, a series of stalks radiating from the top and pointing outward (like points on a crown, but sufficiently blunted to avoid damage to the user's nasal tissues and which improves dispersion of the emitted light), and others.

In preferred embodiments, the wavelengths transmitted through the optic element 30 can be controlled by any suitable means, including for example providing on the base 32 of the fiber optic 30 a coating that acts as a light filter. By selecting an appropriate coating, for example, the optic 30 will deliver only a desired wavelength (or range of wavelengths) light to enter the nasal cavity. Using such coatings or other suitable control, the flash lamp 14 or other light source can be tuned to produce and/or transmit desired light energy, such as in the 600 mm to 700 nm range. Persons of ordinary skill in the art will understand that many methods and apparatus can be used to accomplish the desired non-thermal narrow-band energy transmission and control, including by way of examples and not by way of limitation, use of different gas mixtures within the light source, varying the electrical input, and/or controlling the pulse width. Some lamps themselves can be tuned to produce desired wavelengths for treatment, which can avoid the need for a light filter on the fiber optic 14 or otherwise external to the lamp source.

The invention can include a wide range of other features. By way of example, a safety timeout feature can limit the number of applications of light-therapy to a preset number, after which the unit would shut down for a specified period of time. This can be included in the logic circuitry of by other suitable means, and helps to prevent the user from over-using the device 10.

As indicated above, persons of ordinary skill in the art will understand that the device 10 can be provided with any of a wide range of suitable light sources. Among others, one or more diode lasers can be provided to produce one or more specified wavelengths of light-therapy. For certain embodiments using a diode laser system, there would be no need for any light filters on the fiber optic 30.

Persons of ordinary skill in the art also will understand that the benefits of the invention can be provided in a wide variety of apparatus, including ones other than handheld. Thus, the device 10 can be provided as a small table-top unit (not shown) with AC power and either a flash-lamp or diode laser as the light source. In such embodiments, more than one fiber-optic element may be provided. For example, one fiber-optic can be the longer than the other(s), and can transmit the light from the light source to the other fiber-optic element (which might be similar to element 30 in the attached Figures), with the latter/shorter fiber-optic 30 being the only part that is actually placed inside the user's nasal cavity. Such embodiments would include apparatus at the junction of the two fiber-optic elements to facilitate transmission of the light energy.

Although the methods of the invention are described herein with steps occurring in a certain order, the specific order of the steps, or any continuation or interruption between steps, is not necessarily intended to be required for any given method of practicing the invention. Indeed, although this disclosure focuses on preferred methods and apparatus embodiments, any suitable apparatus or method or process of use or manufacture can be utilized, and still provide at least some of the benefits of the invention.

The apparatus and methods of the present invention have been described with some particularity, but the specific designs, constructions, and steps disclosed are not to be taken as delimiting of the invention. Modifications and further alternatives will make themselves apparent to those of ordinary skill in the art, all of which will not depart from the essence of the invention. All such changes and modifications are intended to be encompassed within the appended claims.

What is claimed is:

1. A method for narrow-band spectrum treatment of nasal membrane inflammation due to seasonal rhinosinusitis, consisting of the steps of:
   providing a handheld narrow-band light emitting device;
   inserting a distal portion of that device into a subject's nostril and positioning that distal portion adjacent the inflamed tissue in the mucosal membrane lining the subject's nasal passage way;
   emitting from that distal portion a series of non-thermal narrow-bandwidth light pulses in the micro-second regime;
   filtering the light pulses so that emitted light wavelengths are within an effective energy range of 600 to 990 nm said range being effective for providing a phototherapeutic effect and preventing tissue damage in the nasal passage way; and
   illuminating the nasal passageways.

2. The method of claim 1, said step of providing a handheld narrow-hand light emitting device including providing at least one safety sensor associated with said device to prevent light emissions when the device is in open space.

3. A method of low level light therapy to treat nasal membrane inflammation due to seasonal rhinosinusitis, consisting of the steps of:
   promoting a tissue anti-inflammatory response in the inflamed nasal tissue while simultaneously preventing tissue damage in the nasal passageway by causing a photo-biostimulation effect solely via a sequential series of narrow-band non-thermal flash lamp emissions from a device inserted into the subject's nasal passageways, wherein said emissions are within the wavelength range of 600 nm to 990 nm.

4. The method of claim 3, in which said device inserted into the subject's nasal passageways includes at least one safety sensor to prevent light emissions when the device is not in a desired position within the subject's nasal passageways.

5. A method of treating seasonal rhinosinusitis consisting of the steps of:
   applying phototherapy and/or photo-biomodulation to a subject's inflamed nasal tissue, the application step including generating and applying visible spectrum light into a user's nasal cavity via an elongated fiber optic element by (a) inserting at least a portion of that optic element into the nasal cavity and (b) administering through that fiber optic element a dosage of approximately 1 to 10 Joules/cm$^2$ of light energy to the user's nasal cavity, said dosage being effective in reducing inflammation of the nasal tissue and preventing tissue damage of the nasal tissue.

6. The method of claim 5, further including the step of providing at least one safety sensor associated with said element, to prevent light emission when the element is not in a desired position within the user's nasal cavity.

\* \* \* \* \*

UNITED STATES PATENT AND TRADEMARK OFFICE
CERTIFICATE OF CORRECTION

PATENT NO. : 9,744,375 B2  
APPLICATION NO. : 14/223861  
DATED : August 29, 2017  
INVENTOR(S) : Richard Oberreiter and Jan Enemaerke Page 1 of 1

It is certified that error appears in the above-identified patent and that said Letters Patent is hereby corrected as shown below:

In the Claims

Column 6, Claim 2, Line 2 should read:
handheld narrow-band light emitting device including pro- Signed and Sealed this
Fourteenth Day of May, 2019

Andrei Iancu
*Director of the United States Patent and Trademark Office*